United States Patent
Hiejima et al.

[11] Patent Number: 6,027,491
[45] Date of Patent: Feb. 22, 2000

[54] SELF-ADMINISTRATION DEVICE FOR LIQUID DRUGS

[75] Inventors: Katsuhiro Hiejima; Takeshi Mori, both of Osaka, Japan

[73] Assignee: Nissho Corporation, Osaka, Japan

[21] Appl. No.: 09/040,291

[22] Filed: Mar. 18, 1998

[30]  Foreign Application Priority Data

Mar. 18, 1997  [JP]  Japan .................................. 9-064879

[51] Int. Cl.⁷ .............................. A61K 9/22; A61M 5/20
[52] U.S. Cl. ...................................... 604/891.1; 604/134
[58] Field of Search ............................. 604/93, 132, 185, 604/890.1–892.1, 153, 246, 143, 134, 133, 131

[56]  References Cited

U.S. PATENT DOCUMENTS

| | | | |
|---|---|---|---|
| 4,312,347 | 1/1982 | Magoon et al. ...................... | 604/143 |
| 4,506,680 | 3/1985 | Stokes ................................. | 604/891.1 |
| 4,713,054 | 12/1987 | Kelly et al. ........................... | 604/89 |
| 4,828,551 | 5/1989 | Gertler et al. ......................... | 604/208 |
| 4,940,460 | 7/1990 | Casey et al. .......................... | 604/143 |
| 5,061,243 | 10/1991 | Winchell et al. ..................... | 604/185 |
| 5,456,679 | 10/1995 | Balaban et al. ...................... | 604/892.1 |
| 5,616,132 | 4/1997 | Newman ............................... | 604/185 |
| 5,697,919 | 12/1997 | Kinoshita et al. .................... | 604/185 |

FOREIGN PATENT DOCUMENTS

| | | |
|---|---|---|
| 0 744 182 A2 | 11/1996 | European Pat. Off. . |
| 2 588 757 | 4/1987 | France . |
| WO 87/00758 | 2/1987 | WIPO . |
| WO 87/00758 A1 | 2/1987 | WIPO . |

*Primary Examiner*—Wynn Wood Coggins
*Assistant Examiner*—Sharon Finkel
*Attorney, Agent, or Firm*—Kubovcik & Kubovcik

[57]  ABSTRACT

A self-administration device for liquid drugs, which can be filled in a short time without troubles such as leakage and is capable of a pushing operation in one-touch. The self-administration device for liquid drugs includes a casing 1; a port portion 2; a reservoir 3 having an open end which is closed by the port portion 2 and is capable of being restored to its original shape; and pushing means 4 for pushing the reservoir 3, wherein the reservoir 3 is pressed by the pushing means 4 to inject the liquid drug. The pushing means 4 includes a cylindrical member inserted slidably into the inner wall of the casing 1, and a spring member housed in the cylindrical member. The cylindrical member and the port position 2 are respectively provided with a male hook 425 and a female hook 25, for acting as detachable mutual engagement means.

4 Claims, 9 Drawing Sheets

SELF-ADMINISTRATION DEVICE FOR LIQUID DRUGS

FIELD OF THE INVENTION

The present invention relates to a self-administation device for liquid drugs (hereinafter referred to as a self-administration device) and, more particularly, to a device for a patient to inject a liquid drug into his or her body to ease pain such as postoperative pain, cancerous pain or the like in combination with or without a system for continuously injecting a very small amount of a liquid drug such as an analgesic or anticancer drug.

BACKGROUND OF THE INVENTION

In the anesthetic field, the control of pains such as postoperative pains, cancerous pains and the like has recently been carried out by epidural catheterization in which a very small amount of liquid drug such as an analgesic is continuously administered to a patient. However, symptoms vary with the patients and patients occasionally complain of a sudden pain even when performing continuous microdose administration of analgesics. In order to cope with such a critical moment, there has been developed a device that is used by a patient for administering a dose of an analgesic to himself or herself. One example of such a device is a patient-controlled analgesic delivery system disclosed in Japanese national publication 63-501195 corresponding to international publication No. W087/00758.

The above patient-controlled analgesic delivery device has, as shown in FIG. 9a, a chamber 90 defined by a raised plateau 98 of a back plate 86 and a flexible circular sheet 96. This chamber 90 is connected to a first conduit communicating with a medical container and a second conduit communicating with a catheter or the like. Arranged on the flexible sheet 96 is a floating plate 100 which limits the volume of the chamber 90. Above the floating plate 100, there is arranged a push button 84 which allows the patient to operate the device by himself or herself. The base portion of the push button 84 is pivoted at its base portion by a pin 116 and biased by a coil spring 124 mounted around the pin 116. When the patient pushes the push button 84, the chamber 90 is depressed by the floating plate 100, as illustrated in FIGS. 9b and 9c, thereby delivering the liquid drug to the body of the patient through the conduit. When the finger is removed from the push button 84, the button 84 is returned to its original state by the coil spring 124, as illustrated in FIG. 9d.

Figure 9:
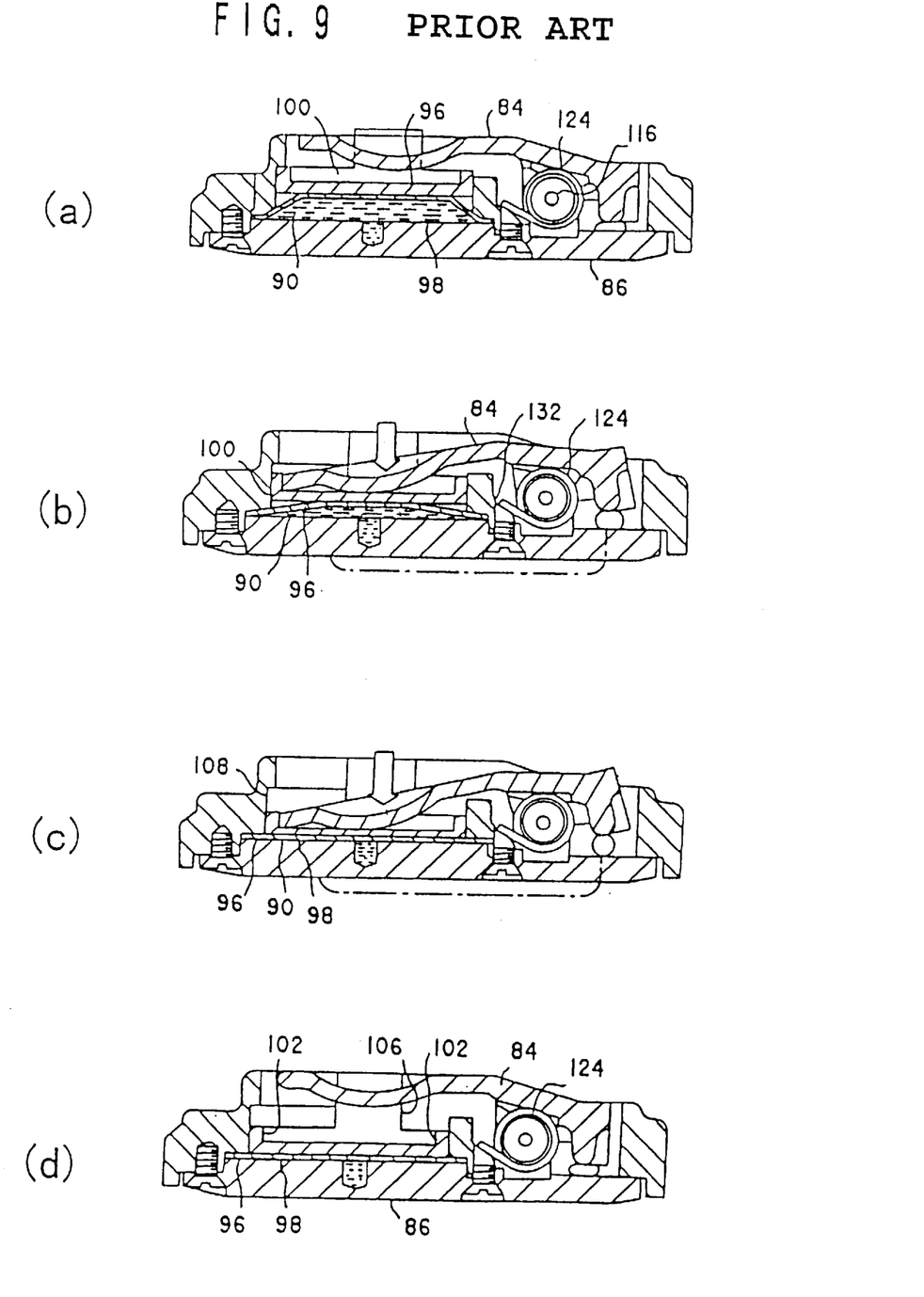
FIGS. 9a–9d are cross sectional views showing the self-administration device for liquid drugs of the prior art.

In the above device, however, the flexible sheet 96 is, as shown in FIG. 9d, not restored to its original state by itself even when the push button 84 is released. Additional liquid drug can be introduced into the chamber 90 only by the pressure of the liquid drug squeezed out of the medical container which is so designed as to send out the liquid drug from a balloon by the restoring force of the balloon. However, it takes a long time to fill up the chamber 90 since the medical container is designed for microdose administration of the liquid drug and thus has a small volume of content. Accordingly, it is difficult to administer an additional dose of the liquid drug. In addition, the above device is limited in dosage to the maximum volume of the reservoir which can not be selected optionally, thus making it difficult to administer the dosage of drug required for the patient in a critical moment. Another problem of the above patient-controlled analgesic delivery device is that it is complex in structure and thus high in manufacturing cost. Further, there is a fear of leakage of the liquid drug from the circumference of the flexible sheet 96, as shown in FIG. 9.

In order to eliminate the aforementioned defects of the conventional device, therefore, we have already proposed a self-administration device for liquid drugs (as disclosed in Unexamined Published Japanese Patent Application No. 8-308925), which comprises: a cylindrical casing having a drug inlet port and a drug outlet port formed at a closed end; a reservoir so housed in the casing as to involve the drug inlet port and the drug outlet port; and pushing means fitted in an open end of the casing, so that when the patient pushes the pushing means, the reservoir is pushed by the pushing means to inject a liquid drug, as reserved in the reservoir, out of the drug outlet port.

Although this device has improved the aforementioned defects of the prior art, the device has such a high conduit resistance that it requires a significant force for injecting the liquid drug when a capillary means such as an epidural catheter is connected for use to the device. Another defect is that it takes a considerable time period to inject the liquid drug completely so that a patient having a declined strength will find it difficult to continue the pushing action of the pushing means. If the pushing means is pushed by a force more than necessary, moreover, the liquid drug may be abruptly injected out of the leading end of the capillary means such as the epidural catheter, and the leading end may go out of position or an excessively high internal pressure may be created in the device or the like to cause the liquid drug to leak.

SUMMARY OF THE INVENTION

It is, therefore, an object of the present invention to provide a self-administration device for liquid drugs, which fills up in a short time, is free from any troubles such as leakage of liquid and is capable of a pushing operation in one-touch.

As a result of assiduous studies for solving the problems in the prior art, the present inventors developed a technical idea of employing a pushing force drive means made of an elastic spring material as the pushing means of the self-administration device for liquid drugs. Based on this technical idea, the present invention was completed. According to the invention, the above object is achieved by providing a self-administration device for liquid drugs, comprising:

a casing having two open ends;

a port portion having a drug inlet port and a drug outlet port, said port portion closing one of the open ends of the casing;

a reservoir having an open end and a closed end, said open end being closed by said port portion, wherein the reservoir is easily deformable by pressing and is capable of being restored to its original shape; and pushing means for pressing the reservoir, the pushing means being slidably fitted in the other open end of the casing, wherein the reservoir is pressed by the pushing means to inject a liquid drug from the drug outlet port.

Further, the pushing means includes: a cylindrical member inserted slidably into the inner wall of the casing; and an elastic spring member housed in the cylindrical member, wherein mutual engagement means are provided between the cylindrical member and the port portion. When the cylindrical member is slid toward the port portion to bring the cylindrical member and the port portion into engagement with each other, the reservoir is pressed by the elastic force of the compressed spring member. Here, in the preferred embodiment, the mutual engagement means is constructed such that when the deformation of the reservoir by the elastic force of the spring member has terminated, the engagement between the cylindrical member and the port portion can be released.

In use, the device may have a construction such that when the cylindrical member is engaged with the port portion, the reservoir is pressed by the elastic force of the compressed spring member, and when the deformation of the reservoir by the elastic force of the spring member is terminated, the engagement between the cylindrical member and the port portion can be released.

Therefor, the pushing means includes: an outer case having a top wall and a skirt portion and having a longitudinal slit formed in said skirt portion; an inner case having a top wall and a skirt portion and having a longitudinal slit formed with an oblique portion at the lower end and rotatably housed in the said outer case, said inner case having male type engagement means protruded from the lower end of the skirt portion; a spring housed in the inner case; and a pushing portion attached to the distal end of the spring. When the inner case and the port portion are engaged with each other and the compressed spring is expanding, a projection formed on the pushing portion is moved along the longitudinal slit of the outer case and the longitudinal slit of the inner case from the upper end position to the lower end position of the overlapping longitudinal running portions.

Alternatively, the device may have a construction wherein the pushing means includes: a cylindrical member having a top wall and a skirt portion and having a longitudinal slit formed with a transversely running portion at its lower end, said cylindrical member having a male engagement portion protruded from the lower end of the skirt portion; a spring housed in parallel with an axis in the cylindrical member; and a pushing portion attached to the distal end of the spring. When the cylindrical mamber and the port portion are engaged with each other and the compressed spring is expanding, a projection formed on the pushing portion is moved along the longitudinal slit of the cylindrical member from the upper end position to the lower end position.

DESCRIPTION OF PREFERRED EMBODIMENTS OF THE INVENTION

Embodiments of the invention are described below with reference to the accompanying drawings.

As shown in FIGS. 1 to 8, a self-administration device for liquid drugs of the invention comprises: a casing 1; a port portion 2; a reservoir 3 having an open end closed by the port portion 2, said reservoir being easily deformable by pressing and restorable to its original shape; and pushing means 4 for pressing the reservoir 3, wherein the reservoir 3 is pressed by the pushing means 4 to inject the liquid drug. The pushing means 4 includes a cylindrical member inserted slidably into the inner wall of the casing 1, and a spring 43 housed in the cylindrical member for acting as an elastic spring member. The cylindrical member and the port portion 2 are respectively provided with a male hook 425 and a female hook 25 which act as detachable mutual engagement means. When the cylindrical member of the pushing means 4 is engaged with the port portion 2, the reservoir 3 is pressed by the elastic force of the compressed spring 43. As the shape of the reservoir 3 deformed by the elastic force of the spring 43 is restored to its original shape, the engagement between the cylindrical member and the port portion 2 can be released.

Figure 1:
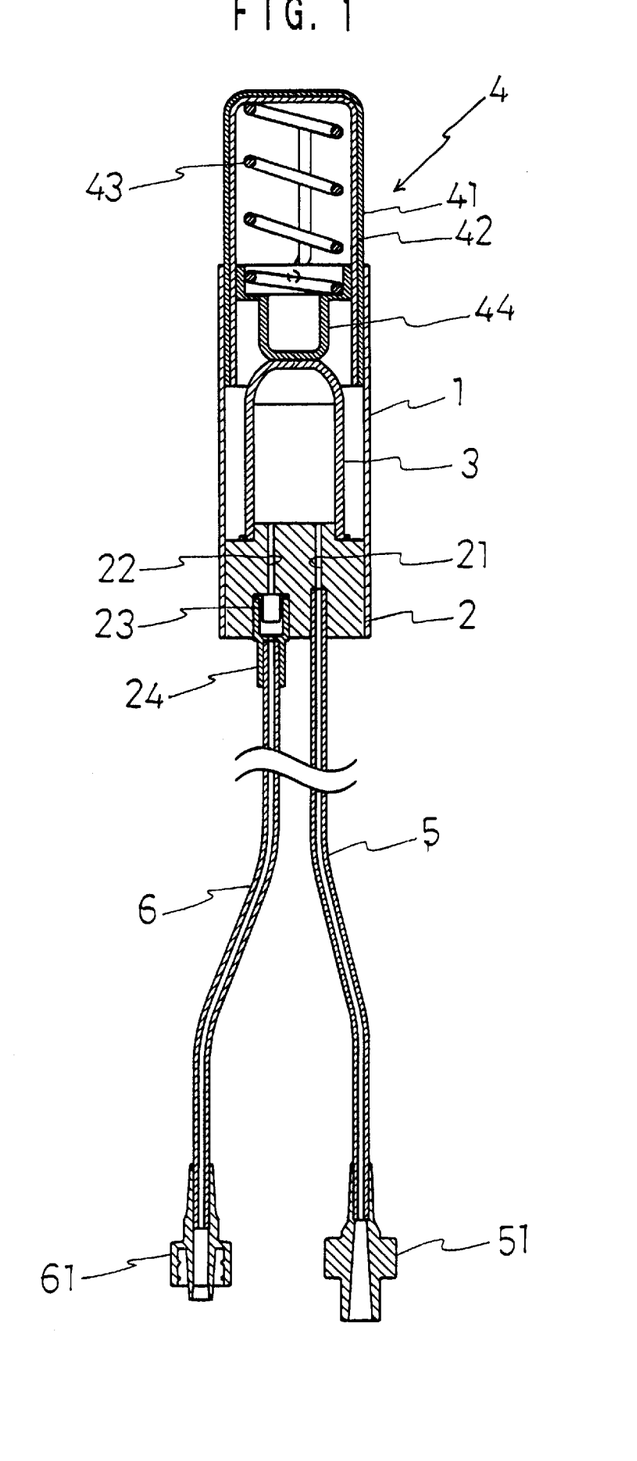
FIG. 1 is a cross sectional view showing a self-administration device for liquid drugs of the present invention.

In the self-administration device for liquid drugs, as shown in FIG. 1, the pushing means 4 includes: the cylindrical member composed of two cylinders of an outer case 41 and an inner case 42; the spring 43 housed in the inner case 42 of the cylindrical member coaxially with the inner case 42; and a pushing portion 44 attached to the distal end of the spring 43. As shown in FIG. 1, the pushing means 4 is slidably provided at one open end side of the casing 1 which is usually formed into a cylindrical shape. In the other open end of the casing 1, moreover, there is provided the port portion 2 which has a drug inlet port 21 and a drug outlet port 22, said port portion 2 closing the other open end of the casing 1. The reservoir 3 is a container which is easily deformable by pressing and capable of being restored to its original shape for temporarily reserving the liquid drug. The reservoir 3 has a closed end and an open end closed by the port portion 2. Here, reference numerals 23 and 24 designate a check valve and a connector, respectively, which are provided at the drug outlet port 22. Numeral 5 designates a drug inlet tube, and numeral 6 designates a drug outlet tube.

The outer case 41 and the inner case 42, composing the cylindrical container of the pushing means 4 have, respectively, top wall 411 and 421 and skirt portions 412 and 422, which respectively have longitudinal slits 413 and 423 extending in the longitudinal (or axial) direction of said cases. The longitudinal slit 423 of the inner case 42 has an oblique portion 424 running in an oblique direction at the lower end. When the inner case 42 is housed in the outer case 41 and the longitudinally running portion of the longitudinal slit 413 is overlapped with that of the longitudinal slit 423, the slits 413 and 423 may have their upper ends aligned, and the lower end of the longitudinal slit 413 of the outer case 41 is positioned at the same level as the lower end (or the lower end of the oblique portion) of the longitudinal slit 423 of the inner case 42. At the lower end of the skirt portion 422 of the inner case 42, there is provided the male hook 425 which can be engaged with the female hook 25 at the upper end of the later-described port portion 2. When the pushing means 4 is slid to a position to contact with the port portion 2, the male hook 425 and the female hook 25 engage with each other.

Figure 2:
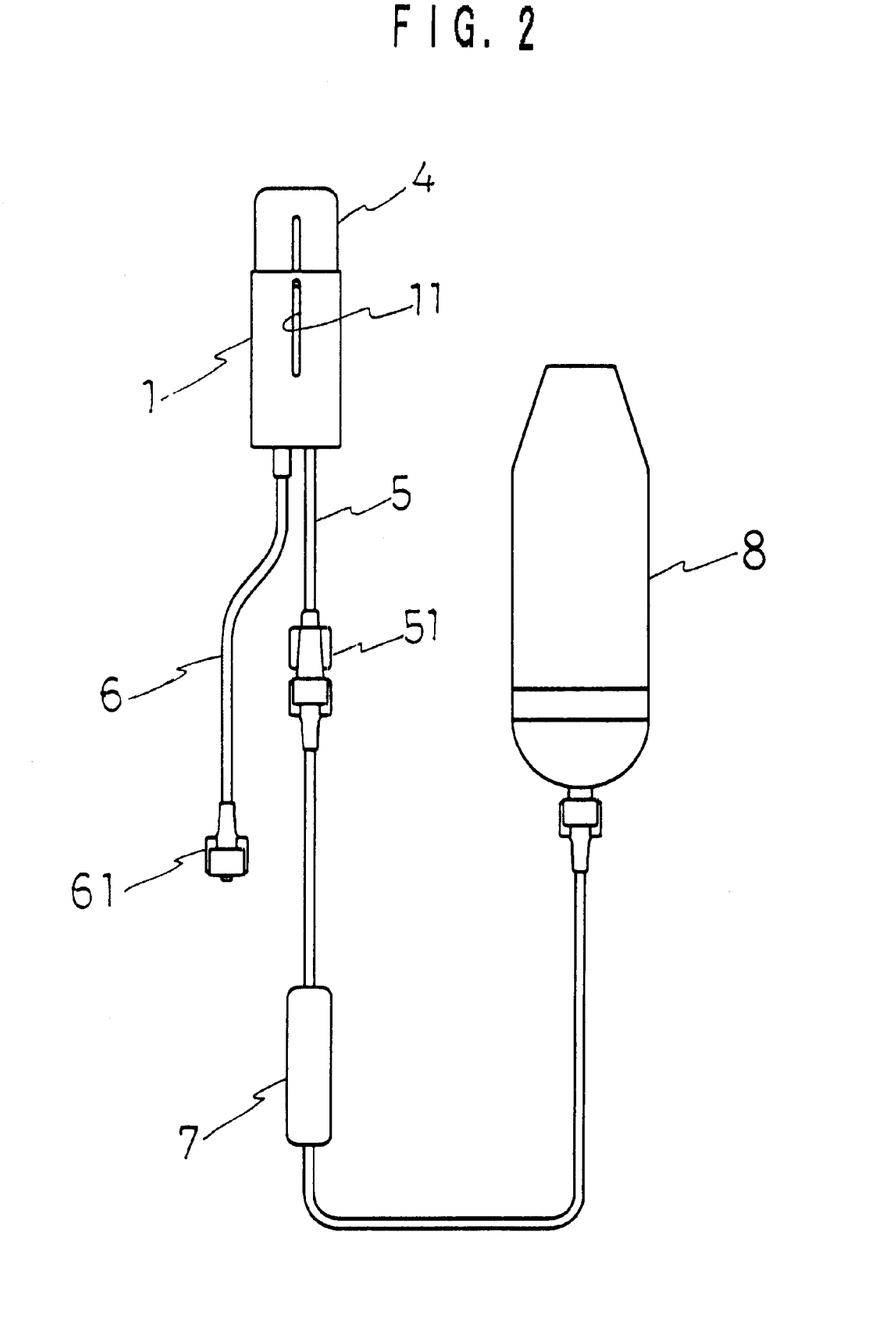
FIG. 2 is a plan view showing the self-administration device for liquid drugs shown in FIG. 1 and a liquid drug container connected thereto through flow control means.

The spring 43 is an elastic spring member which is housed and arranged in the inner case 42 coaxially with the pushing means 4, and which is provided with the pushing portion 44 at its distal end. This pushing portion 44 is arranged adjacent to the closed end of the reservoir 3. The side face of the pushing portion 44 has a projection 441. When the longitudinal slit 413 of the outer case 41, the longitudinal slit 423 of the inner case 42 and a longitudinal slit 11 (as shown in FIG. 2) formed in the side wall of the casing 1 are overlapped in their longitudinally running portions, the projection 441 is movable along the overlapped slits 413, 423 and 11. In this construction, the outer case 41 is not turnable in the casing 1, but the inner case 42 is turned backward by the same distance as the transverse component of the oblique portion 424, when the projection 441 moves downward along the oblique portion 424 of the inner case 42 during pressing of the spring 43 on the reservoir 3. When the projection 441 reaches the lower end portion of the oblique portion 424, the male hook 425 of the inner case 42 and the female hook 25 of the port portion 2 are disengaged from each other. Here, the length of the longitudinal slit 11 of the casing 1 is made equal to or slightly longer than the longitudinal slit 413 of the outer case 41. At the time of assembling the self-administration device for liquid drugs of the invention, therefore, the pushing means 4 is so fitted in one open end of the casing 1 that the projection 441 of the pushing portion 44 may be positioned at the upper end of the longitudinal slit 11.

The other open end of the casing 1 is closed with the port portion 2 which is provided with the drug inlet port 21 and the drug outlet port 22. The reservoir 3 is fitted on the port portion 2 inward of the casing 1 or toward the pushing means 4. The drug inlet port 21 and the drug outlet port 22, respectively, have ends opening in the reservoir 3, and the drug inlet tube 5 and the drug outlet tube 6 are respectively connected to the drug inlet port 21 and the drug outlet port 22, as shown in FIG. 1. A connector 51 of the drug inlet tube 5 can be connected directly or through flow control means 7 to a liquid drug container 8. A connector 61 of the drug outlet tube 6 can be connected to the catheter (not-shown) or the like. Here, the drug outlet port 22 is preferably provided with the connector 24 which has the check valve 23 for preventing the back flow of the liquid drug.

The reservoir 3 temporarily reserves the liquid drug which flows in from the drug inlet port 21. This reservoir 3 is easily deformable by pressing and is capable of being restored to its original shape. To provide flexibility and restorability, the reservoir 3 has a wall thickness of 1 to 2 mm, for example, and is generally made of an elastic material such as silicone rubber or olefin elastomer or natural rubber.

In the present invention, the longitudinal slit 11 of the casing 1 may be replaced by a longitudinal groove (not-shown) formed in the inner wall of the casing 1. On the other hand, the mutual engagement means between the inner case 42 and the port portion 2 may be a female hook (not-shown) provided on the inner case 42 to engage with a male hook (not-shown) formed on the port portion 2. On the other hand, the mutual engagement means of the port portion 2 may be provided on the inner wall of the casing 1.

Figure 6:
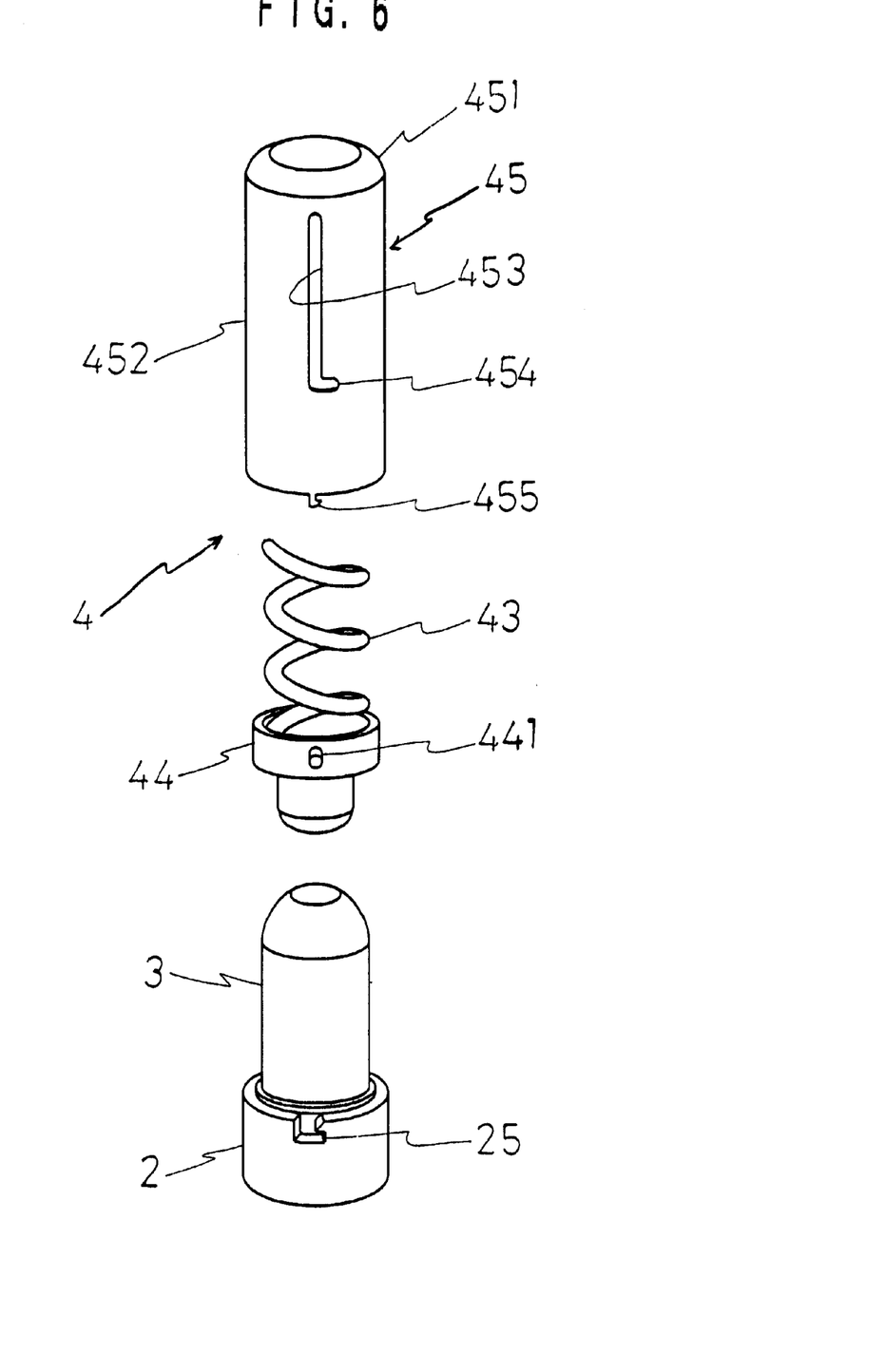
FIG. 6 is an exploded perspective view showing the relationship between pushing means and the reservoir in another embodiment of the self-administration device for liquid drugs of the present invention.

The self-administration device for liquid drugs of the invention may also have a construction as shown in FIG. 6. In this construction, pushing means 40 comprises: a cylindrical member 45; a spring 43 housed in the cylindrical member 45, coaxially with said cylindrical member; and a pushing portion 44 attached to the distal end of the spring 43. As shown in FIG. 6, the construction other than the pushing means 40 is similar to that of the self-administration device for liquid drugs shown in FIG. 1. The cylindrical member 45 has a top wall 451 and a skirt portion 452, which has a longitudinal slit 453. The longitudinal slit 453 is provided at its lower end with a transversely running portion 454. The projection 441 of the pushing portion 44 is movable along the overlapped slits 453 and 11, when the longitudinal slit 453 of the cylindrical member 45 is overlapped with the longitudinal slit 11 (as shown in FIG. 2) formed in the side wall of the casing 1. In this construction, the cylindrical member 45 is not turnable in the casing 1 while the projection 441 is in the longitudinal slit 453. On the other hand, the cylindrical member 45 is turnable backward in the casing 1, by the same distance as that of the transversely running portion 454, when the projection 441 moves downward along the longitudinal slit 453 and reaches to the lower end of the longitudinally running portion 453 during pressing the spring 43 on the reservoir 3. Here, the length of the longitudinal slit 11 of the casing 1 is equal to or slightly longer than the longitudinal slit 453 of the cylindrical member 45. The pushing means 40 is fitted in one open end of the casing 1, so that the projection 441 of the pushing portion 44 may be positioned at the upper end of the longitudinal slit 11.

Below is described how to use the self-administration device for liquid drugs of the invention.

First of all, the use of the self-administration device for liquid drugs, as shown in FIG. 1, will be described with reference to FIGS. 4 and 5.

FIG. 4(a) shows the state of the self-administration device for liquid drugs before pushing the pushing means 4. The projection 441 of the inner case 42 is movable along the longitudinal slits 11, 413 and 423. When the projection moves along the longitudinal slit 11 of the casing 1 and reaches the upper end of the longitudinal slit 11, the outer case 41 is restricted from sliding. In this state, the spring 43 of the pushing means 4 is slightly pressed by the restoring force of the reservoir 3 and by the pressure of liquid drug coming from the drug inlet port 21. At this time, the projection 441 of the pushing portion 44 (as indicated by dotted lines) is positioned at the overlapped lower end of the outer case 41 and the inner case 42 (i.e, the lower end of the oblique portion 424). Moreover, the male hook 425 of the inner case 42 is positioned below the upper end of the longitudinal slit 11 of the casing 1 (e.g., below by the distance between the projection 441 and the male hook 425), as shown in FIG. 5(a). When the self-administration device for liquid drugs is connected to the liquid drug container 8, as shown in FIG. 2, the flow rate of the liquid drug injected to the human body is controlled by the flow control means 7 in this state.

Figure 3:
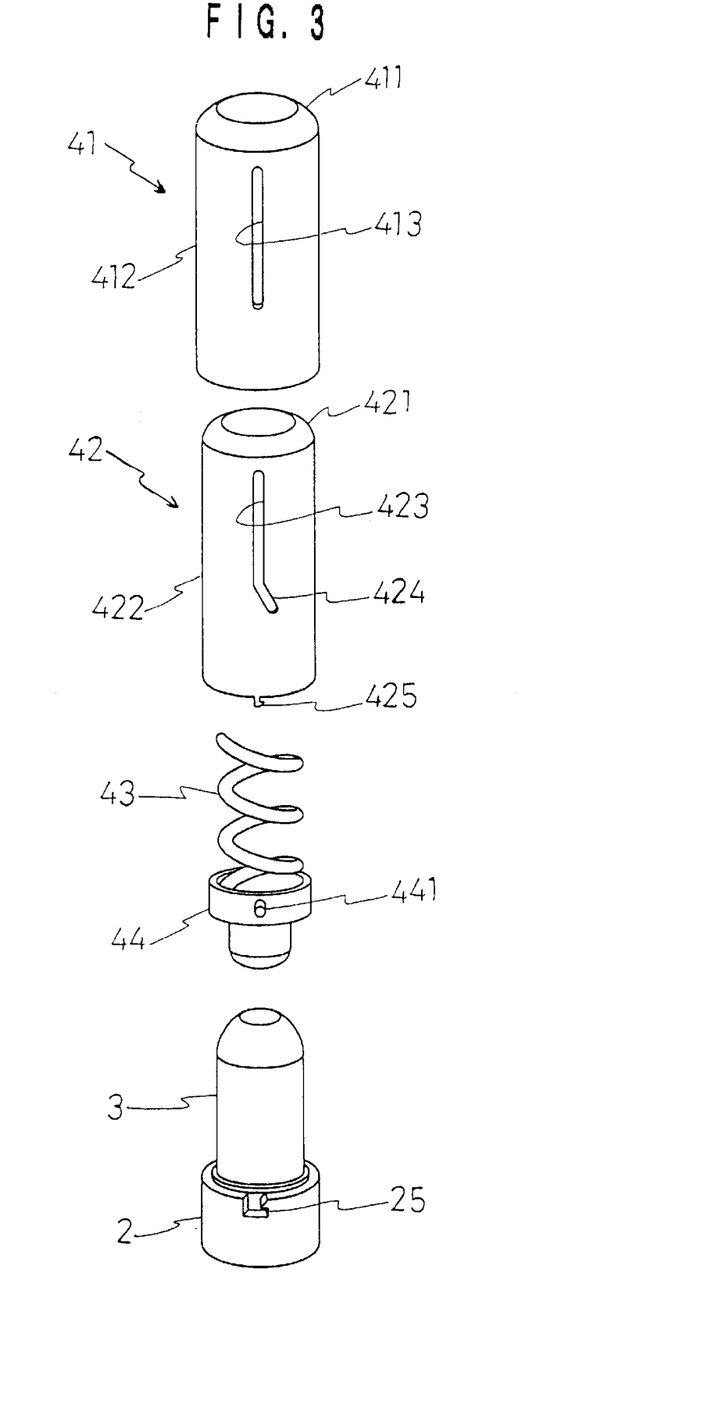
FIG. 3 is an exploded perspective view showing the relationship between the pushing means and the reservoir in the self-administration device for liquid drugs shown in FIG. 1.
Figure 4:
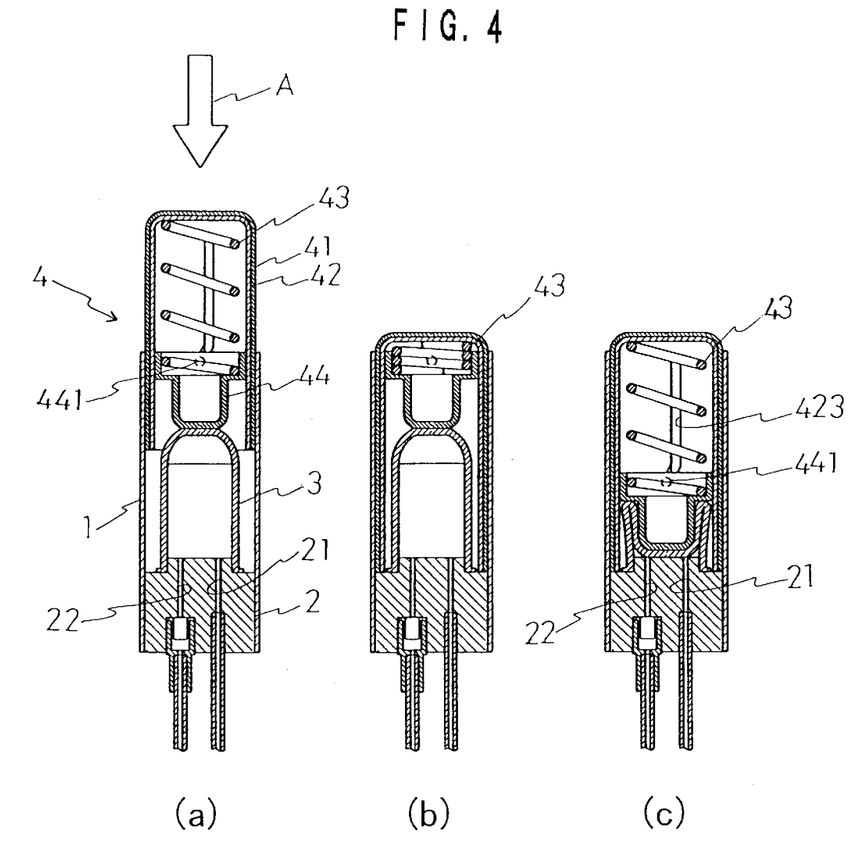
FIGS. 4a–4c are explanatory views showing the relationship between the spring member and mutual engagement means when the pushing means is slid toward the reservoir in the self-administration device for liquid drugs shown in FIG. 1.
Figure 5:
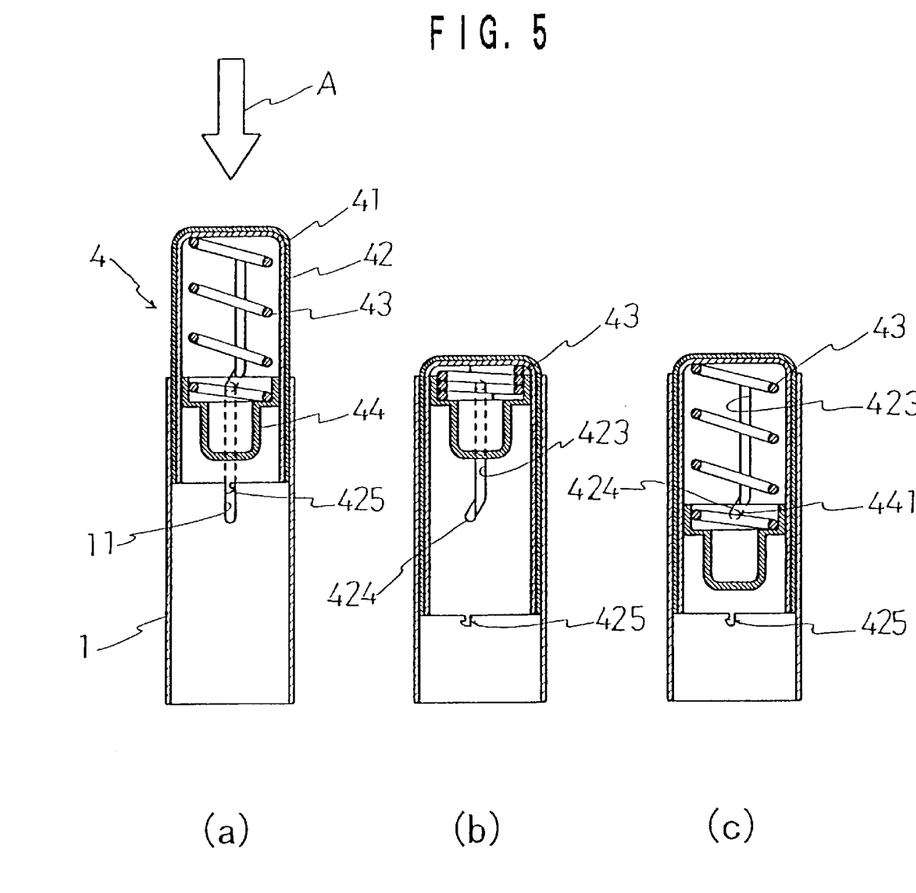
FIGS. 5a–5c are explanatory views showing the relationship between the spring member and mutual engagement means in FIG. 4.

When the pushing means 4 is pushed in the direction of arrow A, as shown in FIG. 4(a), the spring 43 is compressed as is shown in FIG. 4(b), so the liquid drug in the reservoir 3 will not abruptly spurt from the drug outlet port 22. At this time, the male hook 425 of the inner case 42 takes the position, as shown in FIG. 5(b), in which it engages with the female hook 25 (as shown in FIG. 3) of the port portion 2. While the male hook 425 is engaged with the female hook 25, the reservoir 3 is continuously pressed by the spring 43, thus the liquid drug reserved in the reservoir 3 is injected from the drug outlet port 22. At this time, the projection 441 of the pushing portion 44 moves downward along the longitudinal slit 423 of the inner case 42. When the projection 441 moves downward in the oblique portion 424 of the longitudinal slit 423, the inner case 42 turns backward by the same distance as the transverse component of the oblique portion 424. When the projection 441 reaches the lower end position of the oblique portion 424, the male hook 425 of the inner case 42 reaches the position shown in FIG. 5(*c*). When this position is reached by the male hook 425 of the inner case 42, the male hook 425 is disengaged from the female hook 25 of the port portion 2. After the male hook 425 is disengaged from the female hook 25, the spring 43 is pressed by the restoring force of the reservoir 3, or at first, by the pressure of the liquid drug injected from the drug inlet port 21, if the restoring force is weak, then the pushing means 4 is slid to the initial position, as shown in FIG. 4(*a*).

Figure 7:
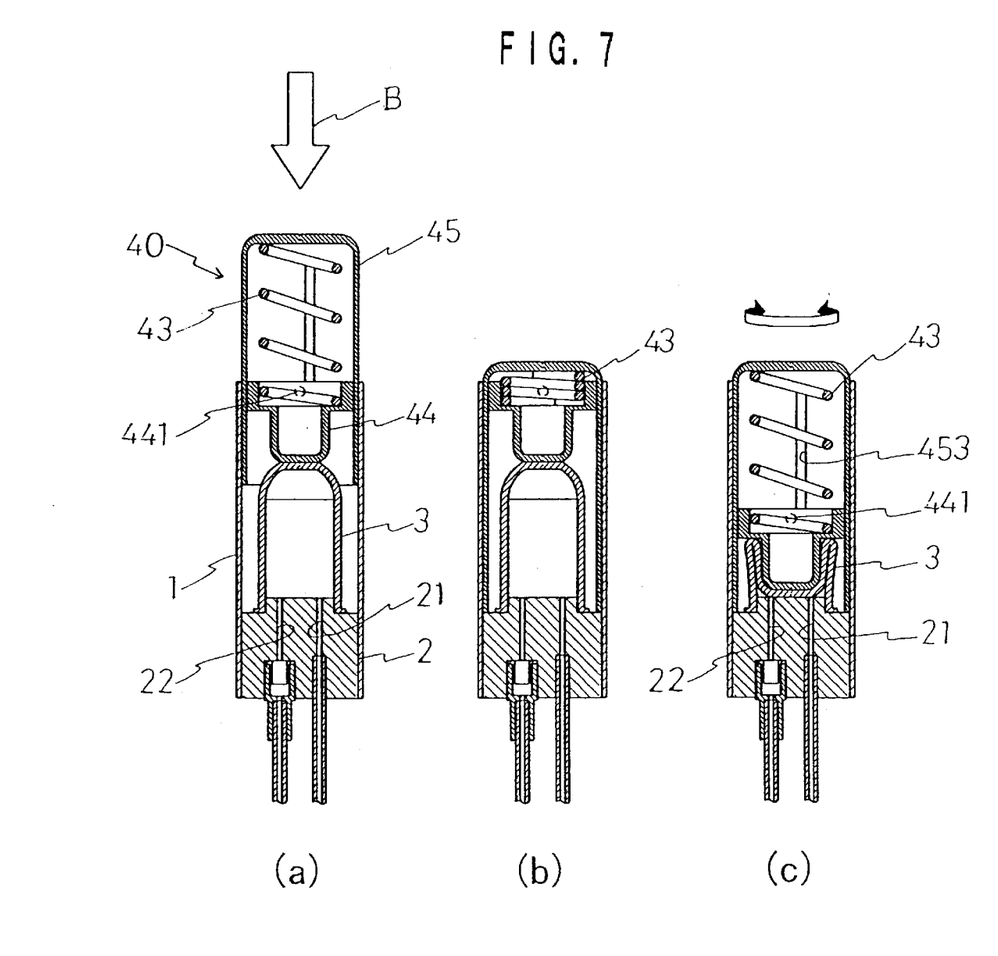
FIGS. 7a–7c are explanatory views showing the relationship between the elastic spring member and the reservoir when the pushing means is slid toward the reservoir in the self-administration device for liquid drugs shown in FIG. 6.
Figure 8:
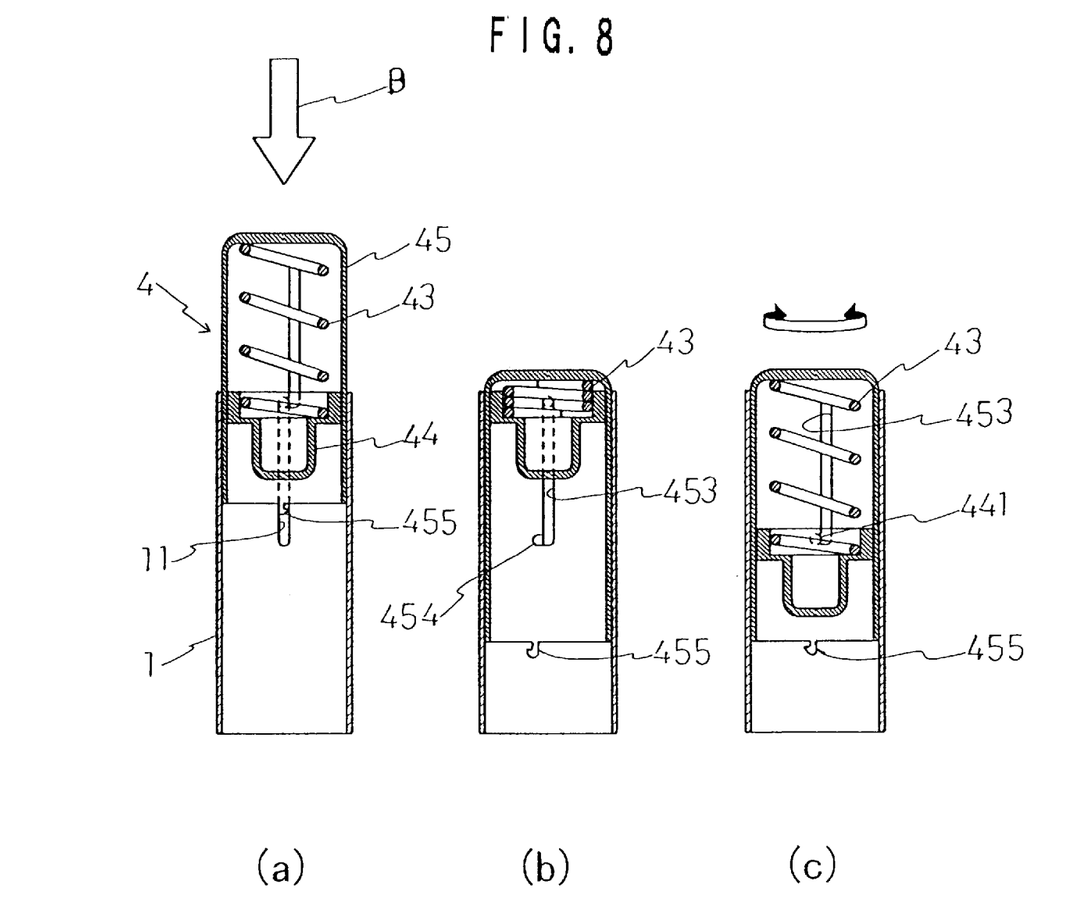
FIGS. 8a–8c are explanatory views showing the relationship between the spring member and mutual engagement means in FIG. 7.

With reference to FIGS. 7 and 8, there will be described how to use the self-administration device for liquid drugs, as shown in FIG. 6.

FIG. 7(*a*) shows the state of the self-administration device for liquid drugs before the pushing means 4 is pushed. When the projection 441 of the pushing portion 44 which moves along the longitudinal slit 11 of the casing 1 reaches the upper end of the longitudinal slit 11, the cylindrical member 45 is restricted from moving upward. In this state, the spring 43 of the pushing means 4 is slightly compressed by the shape retention force of the reservoir 3 and by the pressure of the liquid drug flowing out of the drug inlet port 21. At this time, the projection 441 of the pushing portion 44 (as indicated by dotted lines) is positioned at the lower end of the overlapping cylindrical member 45. Male hook 455 of the cylindrical member 45 is positioned below the upper end of the longitudinal slit 11 of the casing 1, as shown in FIG. 8(*a*).

When the pushing means 4 is pressed in the direction of arrow B, as shown in FIG. 7(*a*), the spring 43 is pressed as is shown in FIG. 7(*b*), so the liquid drug in the reservoir 3 will not abruptly spurt from the drug outlet port 22. At this time, the male hook 455 of the cylindrical member 45 is positioned as is shown in FIG. 8(*b*), and engages with the female hook 25 (as shown in FIG. 6) of the port portion 2. When the male hook 455 is engaged with the female hook 25, the reservoir 3 is continuously pressed by the expanding spring 43, and the liquid drug reserved therein is injected from the drug outlet port 22. When the projection 441 of the pushing portion 44 moves downward along the longitudinal slit 453 and reaches the lower end position of the longitudinal slit 453, the male hook 455 of the cylindrical member 45 takes the position, as shown in FIG. 8(*c*). In this position, when the cylindrical member 45 is turned backward of the direction of the transverse portion 454 of the longitudinal slit 453, the male hook 455 of the cylindrical member 45 can be disengaged from the female hook 25 of the port portion 2. After the male hook 455 is disengaged from the female hook 25, the spring 43 is pushed mainly by the restoring force of the reservoir 3, then the pushing means 4 is slid to the position, as shown in FIG. 7(*a*).

As mentioned above, the self-administration device for liquid drugs of the invention adopts a spring member as the pushing force for pushing the reservoir. When the pushing means is pushed, the spring member acts as a cushion. Therefore, the reservoir is not pressed with more pushing force than necessary, and the reservoir can be pressed by a uniform force, thus the liquid drug will hardly leak. Further, the device is free from troubles such as the distal end of the catheter going out of position, when the self-administration device for liquid drugs of the invention is connected to an epidural catheter.

Moreover, the pushing means can be fixed in the slid (bottom) position, so what is required for the patient is to press the pushing means at first, without continuously pressing the pushing means till the liquid drug is completely injected out of the reservoir. This makes it possible to reduce a charge to the patient.

What is claimed is:

1. A self-administration device for liquid drugs comprising;

a casing having two casing open ends;

a port portion having a drug inlet port and a drug outlet port, the port portion closing one of the casing open ends;

a reservoir provided in said casing and having a reservoir open end and a reservoir closed end, the reservoir open end being closed by the port portion, wherein the reservoir is easily deformable by pressing and can be restored to its original shape; and a pushing means for pressing the reservoir to inject a liquid drug from the drug outlet port, the pushing means being slidably fitted in the other of the casing open ends, wherein the pushing means includes a cylindrical member slidably positioned in the inner wall of the casing and a spring member housed in the cylindrical member; and mutual engagement means provided between the cylindrical member and the port portion;

wherein when the cylindrical member is slid toward the port portion and brought into engagement with the port portion, said reservoir is pressed by the elastic force of the compressed spring member.

2. A self-administration device for liquid drugs according to claim 1, wherein said mutual engagement means is constructed such that when the deformation of the reservoir by the elastic force of the spring member has terminated, the engagement between the cylindrical member and the port portion can be released.

3. A self-administration device for liquid drugs according to claim 2, wherein said pushing means includes:

an outer case having a top wall and a skirt portion and having a longitudinal slit formed in said skirt portion;

an inner case having a top wall and a skirt portion and having a longitudinal slit formed in said skirt portion, an oblique portion formed at the lower end of said longitudinal slit and rotatably housed in the outer case, the inner case having male engagement means protruding from the lower end of the skirt portion;

a spring housed in the inner case; and a pushing portion attached to the distal end of the spring, wherein when the inner case and port portion are engaged with each other, the compressed spring expands and a projection formed on the pushing portion moves along the longitudinal slit of the outer case and the longitudinal slit of said inner case from the upper end position to the lower end position of overlapping longitudinal running portions.

4. A self-administration device for liquid drugs according to claim 2, wherein said pushing means includes:

a cylindrical member having a top wall and a skirt portion and having a longitudinal slit formed in said skirt portion and having a transversely running portion at a lower end, said cylindrical member having a male engagement portion protruding from the lower end of said skirt portion;

a spring housed in said cylindrical member; and a pushing portion attached to a distal end of said spring, and wherein when the cylindrical member and port portion are engaged with each other, the compressed spring expands and a projection formed on said pushing portion moves along the longitudinal slit of said cylindrical member from the upper end position to the lower end position.

* * * * *